(12) United States Patent
Kintrup et al.

(10) Patent No.: US 8,765,991 B2
(45) Date of Patent: Jul. 1, 2014

(54) PROCESS FOR THE PREPARATION OF ISOCYANATES

(71) Applicant: Bayer Intellectual Property GmbH, Monheim (DE)

(72) Inventors: Jürgen Kintrup, Leverkusen (DE); Peter Lehner, Baytown, TX (US); Eric Jakobs, Krefeld (DE); Alfred Soppe, Caojing Shanghai (CN); Knud Werner, Krefeld (DE)

(73) Assignee: Bayer Intellectual Property GmbH (DE)

( * ) Notice: Subject to any disclaimer, the term of this patent is extended or adjusted under 35 U.S.C. 154(b) by 25 days.

(21) Appl. No.: 13/690,425

(22) Filed: Nov. 30, 2012

(65) Prior Publication Data
US 2013/0144081 A1 Jun. 6, 2013

(30) Foreign Application Priority Data
Dec. 2, 2011 (DE) .................. 10 2011 087 654

(51) Int. Cl.
*C07C 249/00* (2006.01)
(52) U.S. Cl.
USPC ........................................ 558/302
(58) Field of Classification Search
USPC ........................................ 558/302
See application file for complete search history.

(56) References Cited

U.S. PATENT DOCUMENTS

| | | | |
|---|---|---|---|
| 3,984,523 A | 10/1976 | Schafer et al. | |
| 4,764,308 A | 8/1988 | Sauer et al. | |
| 2004/0167354 A1 | 8/2004 | Biskup et al. | |
| 2004/0236139 A1 | 11/2004 | Schal et al. | |
| 2006/0099138 A1 | 5/2006 | Walsdorff et al. | |
| 2006/0223966 A1 | 10/2006 | Brodhagen et al. | |
| 2007/0117997 A1 | 5/2007 | Keggenhoff et al. | |
| 2007/0269365 A1 | 11/2007 | Weber et al. | |
| 2007/0276154 A1* | 11/2007 | Haas et al. | 560/347 |
| 2007/0277551 A1 | 12/2007 | Kamper | |
| 2007/0299279 A1 | 12/2007 | Pohl et al. | |
| 2008/0267849 A1 | 10/2008 | Haas et al. | |
| 2010/0160673 A1 | 6/2010 | Bruns et al. | |

FOREIGN PATENT DOCUMENTS

| | | |
|---|---|---|
| DE | 2413358 A1 | 9/1975 |
| DE | 10310888 A1 | 9/2004 |
| DE | 102006023581 A1 | 11/2007 |
| DE | 102006024549 A1 | 11/2007 |
| EP | 0003530 A1 | 8/1979 |
| EP | 0134506 A2 | 3/1985 |
| EP | 0329385 A2 | 8/1989 |
| EP | 1078669 A1 | 2/2001 |
| EP | 1371634 A1 | 12/2003 |
| EP | 1449826 A1 | 8/2004 |
| EP | 1475367 A1 | 11/2004 |
| EP | 1792895 A1 | 6/2007 |
| EP | 2199277 A1 | 6/2010 |
| JP | 2001019405 A | 1/2001 |
| WO | WO-2004/037718 A2 | 5/2004 |
| WO | WO-2007/131700 A1 | 11/2007 |
| WO | WO-2007/134774 A1 | 11/2007 |
| WO | WO-2008/131870 A1 | 11/2008 |
| WO | WO-2010/095927 A1 | 8/2010 |
| WO | WO-2010/149544 A2 | 12/2010 |

* cited by examiner

*Primary Examiner* — Yong Chu
*Assistant Examiner* — Sonya Wright
(74) *Attorney, Agent, or Firm* — Drinker Biddle & Reath LLP

(57) ABSTRACT

The invention relates to a process for the preparation of isocyanates in a system network comprising an isocyanate production plant, a chlorine production plant and a phosgene production plant, in which carbon dioxide formed as a by-product is partially to completely condensed out with the gaseous chlorine formed in the chlorine production plant and enters into the phosgene preparation process and, after the preparation of phosgene, the predominant part of the carbon dioxide formed is thereby sluiced out of the system network in gaseous form.

7 Claims, 4 Drawing Sheets

PROCESS FOR THE PREPARATION OF ISOCYANATES

CROSS-REFERENCE TO RELATED APPLICATIONS

This application claims benefit of German application 10 2011 087 654.5, filed Dec. 2, 2011, which is incorporated herein by reference in its entirety for all its useful purposes.

BACKGROUND OF THE INVENTION

The invention relates to a process for the preparation of isocyanates in a system network comprising an isocyanate production plant, a chlorine production plant and a phosgene production plant, in which carbon dioxide formed as a by-product is partially to completely condensed out with the gaseous chlorine formed in the chlorine production plant and enters into the phosgene preparation process and, after the preparation of phosgene, the predominant part of the carbon dioxide formed is thereby sluiced out of the system network in gaseous form.

In the preparation of isocyanates by phosgenation of the corresponding primary amines, hydrogen chloride gas is formed as a by-product. The hydrogen chloride gas is conventionally contaminated with gaseous substances from the phosgene synthesis or other process stages, such as e.g. carbon oxides (CO and $CO_2$) and phosgene. It can be reused for the preparation of isocyanates by preparing from it chlorine, which is required for the phosgene synthesis.

The preparation of chlorine from hydrogen chloride is adequately known from the prior art. There are various electrolytic processes for the preparation of chlorine which start from hydrochloric acid (HCl (aq.)) or alkali metal chlorides. In addition, direct catalytic oxidation of gaseous hydrogen chloride (HCl (g))

$$4HCl(g) + O_2(g) \rightarrow 2Cl_2(g) + 2H_2O(g),$$

called the Deacon process in the following, is increasingly gaining in importance.

Certain purity requirements are to be imposed on the educt gas stream of a Deacon plant. It is thus known from DE 10 2006 024 549 A1 that the CO content in the intake stream should be less than 1 vol. %, in particular less than 0.5 vol. %, based on the total volume of the intake stream. A higher CO content may impair the plant availability as a result of accelerated catalyst deactivation. It is furthermore known also to add water to the intake stream, in addition to the educts hydrogen chloride and oxygen, in order to smooth the temperature distribution within the catalyst layer (JP 2001 019 405 A). The positive influence of water manifests itself inasmuch as it can at least partly compensate the negative influence of CO. To the extent that the rate of the highly exothermic CO oxidation is slowed down, the metering in of water preferably reduces the development of local hotspots in which the progress of a sintering process which is negative for the activity is preferably accelerated and in which the active component of the catalyst (e.g. ruthenium) is preferably driven out by means of heat. The metering in of water furthermore reduces the formation of volatile metal carbonyl and metal chlorocarbonyl compounds from the catalyst employed, formation of which also already promotes an accelerated discharge of catalytically active metal (e.g. ruthenium) at temperatures below 350° C.

In the sense of a closed production network, it is advantageous to couple a plant for production of chlorine from hydrogen chloride with an isocyanate production plant in order thus to minimize the outlay on apparatus, the energy consumption and therefore the costs by the maximum utilization of circulation flows. In this context chlorine production via a Deacon process is particularly advantageous.

In this connection, however, particular impurities which are contained in a hydrogen chloride stream originating from an isocyanate production may be problematic. There may be mentioned here in particular carbon dioxide, which would become ever more concentrated in the circulation streams if no particular measures were taken.

It is therefore conventional to sluice out carbon dioxide via a suitable purge stream (waste gas stream). In a combined Deacon/isocyanate production plant, this is effected according to the prior art such that the chlorine-rich product stream obtained in the Deacon process is introduced, after drying and compression, into a distillation column. In this context, the overhead condenser of the distillation column is used for chlorine condensation and the bottom evaporator is used for driving out $CO_2$, unreacted oxygen and where appropriate other volatile components. This prior art is known, for example, from EP 0 329 385 A2 or DE 10 2006 023 581 A1. The chlorine separated off can now be fed into the isocyanate process and used for phosgene synthesis.

The gas stream driven out in the chlorine distillation contains the unreacted oxygen (oxygen is conventionally employed in a large excess in the Deacon process), the $CO_2$ and further gaseous substances, and, if necessary after a washing stage, is recycled into the Deacon reaction. By the recycling of the residual gas, a circulation is built up and a concentration of gases, such as e.g. $CO_2$, which must be sluiced out, occurs.

For this, some of the oxygen-containing residual gas recycled into the Deacon reaction is sluiced out of the circulation and the concentration of those gaseous components, which do not further react in the following process stages (such as oxygen) in the circulation stream is thus prevented. The sluicing-out stream must be treated before release into the environment, since is still contains residual chlorine.

The prior art for removal of chlorine from waste gases is a washing with sodium hydroxide solution (see e.g. Ullmann's Encyclopedia of Industrial Chemistry 2006, Chlorine chapter, in particular p. 80, Treatment of Gaseous Effluents), in which the chlorine is absorbed in the wash liquid and reacted chemically:

$$Cl_2 + 2NaOH \rightarrow NaCl + NaOCl + H_2O$$

In order to remove the chlorine reliably, the washing is operated with an NaOH excess. Because of this excess, however, all the $CO_2$ is also removed at the same time:

$$CO_2 + 2NaOH \rightarrow Na_2CO_3 + H_2O$$

This unselective absorption of chlorine therefore has the disadvantage when used in a combined Deacon/isocyanate production plant that in this sodium hydroxide solution is consumed not only for absorption of chlorine, but also for absorption of $CO_2$, which is in itself unnecessary. A further disadvantage is that $Na_2CO_3$ may precipitate out in the wash liquid and block the washer. In such a case the functional capacity thereof no longer exists and the Deacon process must be closed down.

A selective absorption of chlorine from a $CO_2$-containing gas stream, however, has also already been dealt with in several publications. Thus, for example, US H1417 describes a process in which chlorine in absorbed in a wash column with a mixture of sodium thiosulfate ($Na_2S_2O_3$) and sodium hydroxide solution and is reduced. In this context, sodium hydroxide solution is metered in until a pH of approx. 8.5 is established in the wash liquid. At this pH, no NaOH but NaHCO$_3$ is present. This is due to the fact that so little NaOH is fed in that only a part of the CO$_2$ is absorbed, NaHCO$_3$ is formed and this is then consumed in the reduction of the chlorine and the CO$_2$ is liberated again:

$$10CO_2 + 10NaOH \rightarrow 10NaHCO_3$$

$$4Cl_2 + Na_2S_2O_3 + 10NaHCO_3 \rightarrow 8NaCl + 2Na_2SO_4 + 5H_2O + 10CO_2$$

A disadvantage of this procedure is the danger of decomposition of the sodium thiosulfate, during which sulfur precipitates may block the wash column. This decomposition occurs if e.g. the pH of the absorption solution becomes too low locally in the column. For this reason, inter alia, this process is not used on waste gas streams with a relatively high chlorine content and flow rate.

Sulfite is stated as an alternative reducing agent in US H1417, but it is pointed out that sulfite tends to form SO$_2$ particularly readily in the event of variations in the pH. This SO$_2$ would contaminate the gas stream to be purified.

In addition, the use of a reducing agent, whether thiosulfate or sulfite, is expensive.

DE 24 13 358 A1 proposes a multi-stage absorption of chlorine with sodium hydroxide solution, fresh sodium hydroxide solution being led in counter-current to the chlorine- and CO$_2$-containing gas stream. The sodium hydroxide solution is metered in such that it reacts completely with the CO$_2$ to give NaHCO$_3$, which then reacts again with chlorine and thereby liberates the previously bonded CO$_2$:

$$CO_2 + 2NaOH \rightarrow 2NaHCO_3$$

$$Cl_2 + 2NaHCO_3 \rightarrow NaCl + NaOCl + H_2O + 2CO_2$$

A disadvantage of this process is the difficult process procedure refereed to in DE 24 13 358 A1 for complete absorption of chlorine. There is furthermore the danger at a low pH that the hypochlorite reacts further to give the chlorate. Chlorate can be decomposed only with great difficulty, compared with hypochlorite, so that the waste water formed presents a disposal problem. Since also no alkali excess is present, the hypochlorite solution formed is unstable and can easily decompose.

WO 2004/037 718 A2 also describes the removal of substances such as phosgene, solvent residue, CO$_2$ etc. from the hydrogen chloride gas to be employed by absorption in water. The hydrochloric acid formed by this procedure must then be dissociated into hydrogen chloride gas and water in an involved manner, which causes considerable costs.

Summarizing, it therefore remains to be said that the unselective absorption of the chlorine from the CO$_2$-containing purge stream to be sluiced out results in an increased demand for sodium hydroxide solution, while the methods known from the prior art for selective absorption of chlorine from a CO$_2$-containing purge stream have a number of other disadvantages. There was therefore a need for a possibility for sluicing out a gaseous, CO$_2$-containing stream from a combined Deacon/isocyanate production plant without the disadvantages described above thereby occurring.

EMBODIMENTS OF THE INVENTION

An embodiment of the present invention is a process for preparing an isocyanate comprising the steps of
(i) reacting a stream E1 comprising a primary amine with a phosgene-comprising stream P16 to form a product stream P1, which comprises said isocyanate, hydrogen chloride, unreacted phosgene, and carbon oxides;
(ii) separating the product stream P1 into a liquid product stream P2 comprising said isocyanate and a gaseous product stream P3 comprising hydrogen chloride, unreacted phosgene, and carbon oxides;
(iii) mixing the product stream P3 with a gaseous product stream P4 comprising oxygen to form a gaseous mixed stream P5;
(iv) oxidizing the gaseous mixed stream P5 on a catalyst to form a gaseous product stream P6 comprising hydrogen chloride, carbon dioxide, excess oxygen, chlorine, and water;
(v) partially to completely removing the hydrogen chloride and water from stream P6 as a stream P7 comprising hydrochloric acid to form a product stream P8 depleted in hydrogen chloride and water;
(vi) separating the product stream P8 into a liquid chlorine-rich product stream P9, which comprises chlorine, carbon dioxide, and oxygen, and a gaseous, low-chlorine product stream P10, which comprises the residual amount of chlorine from P8 not contained in P9, carbon dioxide, and oxygen;
(vii) dividing the gaseous product stream P10 into a gaseous purge stream P11 and a gaseous product stream P12;
(viii) treating the purge stream P11 with an aqueous base E3 to form a gaseous purge stream P13 and a liquid waste water stream P14;
(ix) mixing the gaseous stream P12 with a gaseous stream E4 comprising oxygen to form the gaseous product stream P4 which comprises oxygen and is employed in step (iii);
(x) evaporating the liquid chlorine-rich product stream P9 to form a gaseous chlorine-rich product stream and mixing the gaseous chlorine-rich product stream with carbon monoxide E5 and with chlorine E6 to give a mixture, and reacting said mixture to give a gaseous product stream P15 comprising phosgene and carbon oxides;
(xi) separating the gaseous product stream P15 in a separating device I into a phosgene-rich product stream P16, which is employed in step (i) and comprises phosgene and carbon oxides, and into a low-phosgene purge stream P17 which comprises the residual amount of the phosgene from P15 which is not contained in P16 and carbon oxides;
wherein
in step (vi) the separation of the product stream P8 into a liquid chlorine-rich product stream P9 and into a gaseous low-chlorine product stream P10 is carried out by cooling P8 to a temperature of from −10° C. to −80° C. under an absolute pressure of from 1 bar to 30 bar without subsequent distillation.

Another embodiment of the present invention is the above process, wherein, in step (xi), from 35% to 99% of the total carbon dioxide to be sluiced out is sluiced out via the purge stream P17.

Another embodiment of the present invention is the above process, wherein, in step (ii), P1 is divided into the liquid product stream P2 comprising said isocyanate and a gaseous stream, wherein a portion of said gaseous stream is sluiced out and passed into a hydrogen chloride absorber, and wherein the remaining portion of said gaseous stream is treated further as stream P3 in step (iii).

Another embodiment of the present invention is the above process, wherein, in step (v), the partial to complete removal of the hydrogen chloride and of the water from P6 is realized by treatment of P6 with an absorption agent chosen from water or 1 to 20% strength hydrochloric acid.

Another embodiment of the present invention is the above process, wherein, in step (vii), the gaseous product stream P10 is divided into a gaseous purge stream P11 and into a gaseous product stream P12 in a weight ratio of P12:P11 averaged over time of from 100:1 to 5:1.

Another embodiment of the present invention is the above process, wherein, in step (viii), an aqueous alkali metal or alkaline earth metal hydroxide solution is used as the aqueous base E3.

Another embodiment of the present invention is the above process, wherein the gaseous product stream P12 is led through a wash in which the gas is washed and only thereafter is mixed in step (ix) with a gaseous stream E4 comprising oxygen.

DETAILED DESCRIPTION OF THE INVENTION

The present invention provides a process for the preparation of an isocyanate comprising the steps (i) reaction of a stream E1 containing a primary amine with a phosgene-containing stream P16 in a reactor A to form a product stream P1, which includes the desired isocyanate, hydrogen chloride, unreacted phosgene and carbon oxides, (ii) separation of the product stream P1 in a separating device B into a liquid product stream P2 including the isocyanate and a gaseous product stream P3 including hydrogen chloride, unreacted phosgene and carbon oxides, (iii) mixing of the product stream P3 including hydrogen chloride, unreacted phosgene and carbon oxides with a gaseous product stream P4 including oxygen to form a gaseous mixed stream P5, (iv) oxidation of the gaseous mixed stream P5 on a catalyst in an oxidative process stage C to form a gaseous product stream P6 which includes hydrogen chloride, carbon dioxide, in particular the carbon dioxide from P5 and carbon dioxide formed by oxidation of carbon monoxide and phosgene, excess oxygen, chlorine and water, (v) partial to complete removal of the hydrogen chloride and the water from P6 as a stream P7 containing hydrochloric acid by treatment of P6 with an absorption agent E2, preferably with water or 1 to 20% strength hydrochloric acid, preferably 4 to 18% strength hydrochloric acid, particularly preferably 4 to 15% strength hydrochloric acid, in a separating device D to form a product stream P8 depleted in hydrogen chloride and water, preferably 70% to 100% of the hydrogen chloride contained in P6 and 99.00% to 100%, preferably 99.99% to 100%, particularly preferably 100% of the water contained in P6 being removed from this stream, (vi) separation of the product stream P8 in a separating device E into a liquid chlorine-rich product stream P9, which includes chlorine, and indeed preferably 50% to 100% of the chlorine from P8, carbon dioxide and oxygen, and into a gaseous, low-chlorine product stream P10, which includes the residual amount of the chlorine from P8 not contained in P9 and carbon dioxide and oxygen, it also being possible for P9 and/or P10 additionally to contain hydrogen chloride which has not been removed in step (v), (vii) division of the gaseous product stream P10 into a gaseous purge stream P11 and into a gaseous product stream P12, preferably in a weight ratio P12:P11 averaged over time of from 100:1 to 5:1, particularly preferably from 50:1 to 10:1, it being possible for the division of P10 to be effected continuously or intermittently, i.e. at intervals (as soon as gases to be sluiced out have concentrated in a relatively large amount), (viii) treatment of the purge stream P11 with an aqueous base E3, preferably with an aqueous alkali metal or alkaline earth metal hydroxide solution, particularly preferably sodium hydroxide solution, in a waste gas treatment stage F to form a gaseous purge stream P13 and a liquid waste water stream P14, (ix) mixing of the gaseous stream P12 with a gaseous stream E4 including oxygen to form the gaseous product stream P4 which includes oxygen and is employed in step (iii), (x) evaporation of the liquid chlorine-rich product stream P9 in an evaporator G, mixing of the gaseous chlorine-rich product stream obtained in this way with carbon monoxide E5 and chlorine E6 and reaction of the mixture obtained in this way in a reactor H to give a gaseous product stream P15 including phosgene and carbon oxides, (xi) separation of the gaseous product stream P15 in a separating device I into a phosgene-rich product stream P16, which is employed in step (i), and includes phosgene, and indeed preferably 70% to 100% of the phosgene from P15, and carbon oxides, and into a low-phosgene purge stream P17 which includes the residual amount of the phosgene from P15 which is not contained in P16 and carbon oxides, wherein in step (vi) the separation of the product stream P8 into a liquid chlorine-rich product stream P9 and into a gaseous low-chlorine product stream P10 is carried out by cooling P8 to a temperature of from −10° C. to −80° C. under an absolute pressure of from 1.0 bar to 30 bar without subsequent distillation.

In the context of this invention, the term product stream designates a stream which essentially contains a valuable product (or several valuable products) obtained in a process step, whether an end product or intermediate product (i.e. educt for a further process step). This is distinguished from the term purge stream, which designates a stream which essentially contains troublesome components which are to be sluiced out of the overall process, such as the carbon dioxide mentioned. According to the invention, the term carbon oxides includes both carbon monoxide and carbon dioxide.

Preferred primary amines are those chosen from the group consisting of aliphatic amines (preferably 1,6-diaminohexane, methylamine, ethylamine, propylamine, butylamine, pentylamine and hexylamine, particularly preferably 1,6-diaminohexane), cycloaliphatic amines (preferably cyclohexylamine, isophoronediamine, 4,4'-diaminodicyclohexylmethane, 2,4'-diaminodicyclohexylmethane, 2,2'-diaminodicyclohexylmethane and mixtures of the diaminodicyclohexylmethane isomers, particularly preferably isophoronediamine, 4,4'-diaminodicyclohexylmethane, 2,4'-diaminodicyclohexylmethane, 2,2'-diaminodicyclohexylmethane and mixtures of the diaminodicyclohexylmethane isomers), araliphatic amines (preferably benzylamine), and aromatic amines (preferably aniline, chloroaniline, toluylenediamine, 1,5-diaminonaphthalene, 4,4'-diaminodiphenylmethane, 2,4'-diaminodiphenylmethane, 2,2'-diaminodiphenylmethane, mixtures of the diaminodiphenylmethane isomers and mixtures of the diaminodiphenylmethane isomers and higher homologues thereof [also generally called e.g. MDA, PMDA, polymer-MDA or di- and polyamines of the diphenylmethane series, i.e. mixtures of di- and polyamines, such as are obtained from the acid-catalysed condensation of aniline and formaldehyde], particularly preferably toluylenediamine).

In this context, the reaction of the primary amines with phosgene to give the corresponding isocyanates in step (i) can in principle be carried out by all the processes known in the prior art. Gas and liquid phase processes are conceivable in this context. Liquid phase processes are carried out in the presence of a solvent which is inert under the reaction conditions. In gas phase processes, the product stream is liquefied after the reaction by passing it through an inert solvent or spraying in an inert solvent. Examples of suitable liquid phase processes are described in US-A 2007/0299279 and DE-A 103 10 888. Examples of suitable gas phase processes are described in EP 1 449 826 A1 and EP 2 199 277 A1.

According to the invention, suitable reactors A in this context are in principle all the reactor types known to the person skilled in the art for phosgenation reactions, e.g. tube reactors. Suitable reactors are described, for example, in DE-A 103 10 888 and US-A 2007/0299279.

Devices known to the person skilled in the art for distillation and/or absorption are preferably employed as the separating device B in step (ii). The stream P2 containing isocyanate obtained in step (ii) is worked up by one of the conventional processes in the prior art and is in this way brought to the purity necessary for the desired subsequent use of the isocyanate. Examples of the purification of crude isocyanates are described e.g. in EP 1 371 634 A1, EP 1 078 669 A1, EP 1 475 367 A1, EP 1 792 895 A1, WO 2010/095927 A1, WO 2010/149544 A2 and the literature references cited there.

The product stream P3 obtained in step (ii) also additionally typically contains, alongside hydrogen chloride gas, the following constituents:
hydrocarbons and chlorohydrocarbons up to 20 vol. % in total, preferably up to 3.0 vol. % in total, particularly preferably up to 1.0 vol. % in total, up to 1.0 vol. %, preferably 0.010 vol. % to 0.10 vol. % of aromatic hydrocarbons and aromatic chlorohydrocarbons being contained therein,
carbon oxides, nitrogen and further inert gases up to 10 vol. % in total, preferably up to 5.0 vol. % in total,
phosgene up to 1.0 vol. %, preferably up to 0.50 vol. %.

According to the invention, the oxidation of the gaseous mixed stream PS containing hydrogen chloride obtained in step (iii) is carried out in a Deacon process in step (iv). In this context, the reaction temperature is preferably 150° C. to 500° C., and the reaction pressure is 1.0 bar (abs.) to 25 bar (abs.).

Catalysts which are preferably to be employed contain ruthenium compounds, which are applied, in particular, to supports. Suitable support materials and/or binders for the support are in particular, for example, silicon dioxide, graphite, titanium dioxide having the rutile or anatase structure, tin dioxide, zirconium dioxide, aluminium oxide or mixtures thereof, preferably titanium dioxide, zirconium dioxide, aluminium oxide or mixtures thereof, particularly preferably γ- or δ-aluminium oxide or mixtures thereof. Aluminium oxide or zirconium oxide is the preferred binder. The content of binder can be, based on the finished catalyst, 1 to 30% by weight, preferably 2 to 25% by weight and very preferably 5 to 20% by weight. The binder increases the mechanical stability (strength) of the catalyst shaped bodies.

The activity of the catalysts can be variable or constant in the flow direction of the gas stream to be oxidized. The reaction can be carried out in fixed, flow or fluidized beds in one or more stages in succession. The reaction procedure can be carried out isothermally, quasi-isothermally or adiabatically with intermediate cooling, discontinuously or continuously. If several reaction stages are used, the educts can be added completely before the first reactor or in distribution over each reactor. It is also possible for an educt, preferably the product stream P4 including oxygen, to be added before the first reactor, and for the second educt, preferably the product stream P3 including the hydrogen chloride gas, to be fed in distribution over each reactor. The oxygen is expediently employed in excess with respect to the hydrogen chloride gas, it being possible for excesses of 100% of the sto-ichiometric amount and more to be employed. Excesses of oxygen of between 100% and 300% of the stoichiometric amount are preferred. The impurities contained in the stream P3 including hydrogen chloride, such as CO and phosgene, are likewise oxidized in step (iv) and form $CO_2$. Preferably, this oxidation takes place completely, so that the stream P6 no longer contains significant amounts of carbon monoxide and phosgene. After the reaction, a gas mixture P6 is therefore preferably present, which contains, in addition to chlorine, water and the excess oxygen, only still unreacted hydrogen chloride gas and carbon dioxide.

In the subsequent step (v), the hydrogen chloride gas is first separated out together with the majority of the water of reaction. This is preferably effected in a quench process or an absorption step or a combination of the two. In this context, the temperature is preferably 15° C. to 150° C. and the pressure is preferably 1.0 bar (abs.) to 25 bar (abs.) and is particularly preferably the same as in reaction step (iv). The separating device D employed is preferably a multi-stage device which comprises a quench and downstream of this at least one absorber. The absorption agent E2 employed is preferably water or dilute hydrochloric acid, concentrated hydrochloric acid being formed as a by-product. It is also possible to employ other absorption agents. Organic substances, such as tertiary amines or heteroaromatics, or also ionic liquids are preferably possible. The water of reaction is then virtually completely removed in a drying step. For this, a column charged with concentrated sulfuric acid is preferably used. It is also possible to employ other, solid drying agents, preferably zeolites or also aluminium oxides.

The separating device E employed in step (vi) is e.g. a device for condensation of gases, but not a distillation apparatus. All the conventional condensers in the prior art can in principle be employed. Preferably, the condensation temperature is in a range of from −80° C. to 0° C., depending on the pressure. The liquid chlorine-rich product stream P9 obtained in this way preferably contains 70 mol % to 100 mol % of chlorine, 0 mol % to 2.0 mol % of oxygen, 1.0 mol % to 30 mol % of carbon dioxide and 0 mol % to 20 mol % in total of one or more of the substances of the group of noble gases, inert substances, carbon monoxide and hydrogen chloride.

In the division of the product stream P10 carried out in step (vii), the composition thereof is not changed; this step is merely a division of the stream P10 into two part streams P11 and P12, the composition of which is in each case the same as that of P10. In a weight ratio averaged over time means in this context that P12 and P11, averaged over a production cycle, are preferably divided in a ratio of between 100:1 and 5:1, particularly preferably of from 50:1 to 10:1. This is to be noted in the event of intermittent sluicing out of the purge stream P11.

The waste gas treatment stage F employed in step (xiii) is preferably an absorption column in which the chlorine contained in the part stream P11 and the hydrogen chloride are washed out with sodium hydroxide solution.

The stream E4 including oxygen fed into step (ix) can be any desired gas stream which contains oxygen, and indeed preferably at least 80% by weight of oxygen, based on the total weight of E4, the other constituents of which do not interfere in the subsequent process steps (for example E4 can contain noble gases or nitrogen in addition to oxygen). Preferably, oxygen in a purity of at least 90% is employed as stream E4.

In step (x), in principle all evaporator types known from the prior art can be employed as the evaporator G. Evaporators with vertical tube bundles or vertical bayonet tubes are preferred. Examples of suitable evaporators are to be found in *Design and Operation of Chlorine Vaporisers* (Euro Chlor Publication GEST 75/47, draft 9th edition, October 1999, p. 1 to 49). The reactor H used for the preparation of phosgene is preferably a tube bundle reactor. Examples of suitable reactors are to be found in Ullmann's Encyclopedia of Industrial Chemistry, DOI 10.1002/14356007.a19_411, Wiley-VCH 2005, Phosgene chapter, in particular p. 3 (Process Description). For preparation of the phosgene, fresh chlorine E6, in addition to carbon monoxide, is fed to the gaseous chlorine-rich product stream in order to compensate previous chlorine losses (for example due to incomplete conversion of hydrogen chloride in the oxidative process stage C), and indeed preferably 5% to 50% of the chlorine stream fed via the evaporator G. Carbon monoxide is preferably employed in excess, and indeed preferably in an excess of from 1.0% to 20% of theory (see e.g. EP 0 003 530 A1 and EP 0 134 506 A2).

The separating device I employed in step (xi) is preferably a condenser or a distillation apparatus followed by an absorber (see e.g. Ullmann's Encyclopedia of Industrial Chemistry, DOI 10.1002/14356007.a19_411, Wiley-VCH 2005, Phosgene chapter, in particular p. 3, FIG. 1); a condenser with a downstream absorber is particularly preferably employed. The phosgene formed is removed there by liquefaction and absorption of carbon dioxide and excess carbon monoxide and where appropriate other inert gases present. A part of the carbon dioxide (preferably between 10% and 70% of the carbon dioxide contained in P15) is thereby also condensed. The gas phase which remains and contains carbon monoxide and the residual part of the carbon dioxide is passed into a waste gas treatment stage and enters from there into the open, so that carbon dioxide is sluiced out of the system network by this route. In a preferred embodiment, 35% to 99%, preferably 40% to 95% of the total carbon dioxide to be sluiced out is sluiced out via the purge stream P17.

By the procedure according to the invention in step (vi), the majority of the carbon dioxide accordingly is not removed via a sluicing-out stream from the oxygen-containing residual gas led back into the Deacon reaction, as was hitherto conventional in the prior art. Rather, the carbon dioxide is mostly removed by condensation together with the chlorine. It therefore cannot become concentrated in the gas stream P10 led back in. Sluicing out of a part stream P11 from this gas stream is then still necessary only for removing other components, such as e.g. nitrogen or argon. The stream P11 still contains, in addition to residues of chlorine, only a small amount of carbon dioxide, which, however, is no longer of importance, since only insignificantly more aqueous base E3 is consumed by this.

In the preparation of phosgene in the reactor H, carbon dioxide is inert and does not impair the reaction.

The chlorine-rich product stream P9 can also be fed to other fields of use in addition to the preparation of phosgene if increased carbon dioxide contents do not interfere in the planned field of use.

The process according to the invention can also comprise further steps in addition to the (i) to (xi) mentioned (for example the compression of gas streams or the purification or drying of a product stream before use thereof in the next process step), which for simplification of the description have not been mentioned expressly above because they do not relate to the core of the invention.

BRIEF DESCRIPTION OF THE DRAWINGS

The invention is explained further in more detail in the following with the aid of FIGS. 1 to 4.

For clarity, the same designations for substance streams are used in all the figures, e.g. the crude product of the phosgenation in reaction A is always designated P1, even though its exact composition can vary according to the plant construction.

FIG. 1:

The product stream P1 obtained in the preparation of isocyanate in reactor A is separated in the separating device B into the isocyanate-containing product stream P2 and the gas stream P3. P3 is provided as a crude gas stream containing hydrogen chloride and contains, in addition to hydrogen chloride, inter alia contents of carbon dioxide, carbon monoxide and phosgene which has not reacted in reactor A.

P3, after mixing with the oxygen-containing stream P4 is fed as P5 to the Deacon reaction (C). C is configured as a cascade of adiabatically operated reactors with intermediate cooling. In this context, the majority of the hydrogen chloride is reacted on a heterogeneous ruthenium catalyst to give chlorine and water. In side reactions, the carbon monoxide contained in the gas stream P3 and phosgene are reacted to give carbon dioxide and chlorine. The unreacted hydrogen chloride and the majority of the water produced in the emerging product stream P6 are removed from the product gas P6 in a separating device D as hydrochloric acid P7. For this, additional fresh water or dilute hydrochloric acid (stream E2) is fed to the separating device D.

The product gas stream P8 obtained in this way is separated in a subsequent separating device E into a liquid, chlorine-rich rich product stream P9 and a gaseous, low-chlorine product stream P10 by condensation. The liquid stream P9 is saturated with dissolved oxygen, according to the partial pressure of oxygen in the gas phase.

Downstream of the separating device E, a part stream P11 is sluiced out of the remaining gas stream P10. This part stream still contains chlorine and a residual amount of carbon dioxide and must be led into a waste gas treatment stage F, in which the chlorine is removed with a stream E3 containing sodium hydroxide solution. The purified gas stream P13 then leaves the plant. The waste water stream P14 contains the chlorine removed in a chemically bonded form as hypochlorite and chloride, and the carbon dioxide as carbonate.

The gas stream P12 remaining after the sluicing out is mixed with a fresh oxygen stream E4 as a replacement for the oxygen consumed in the process. The stream P4 obtained in this way is then combined, as described above, with the gas stream P3 containing hydrogen chloride.

Figure 1:
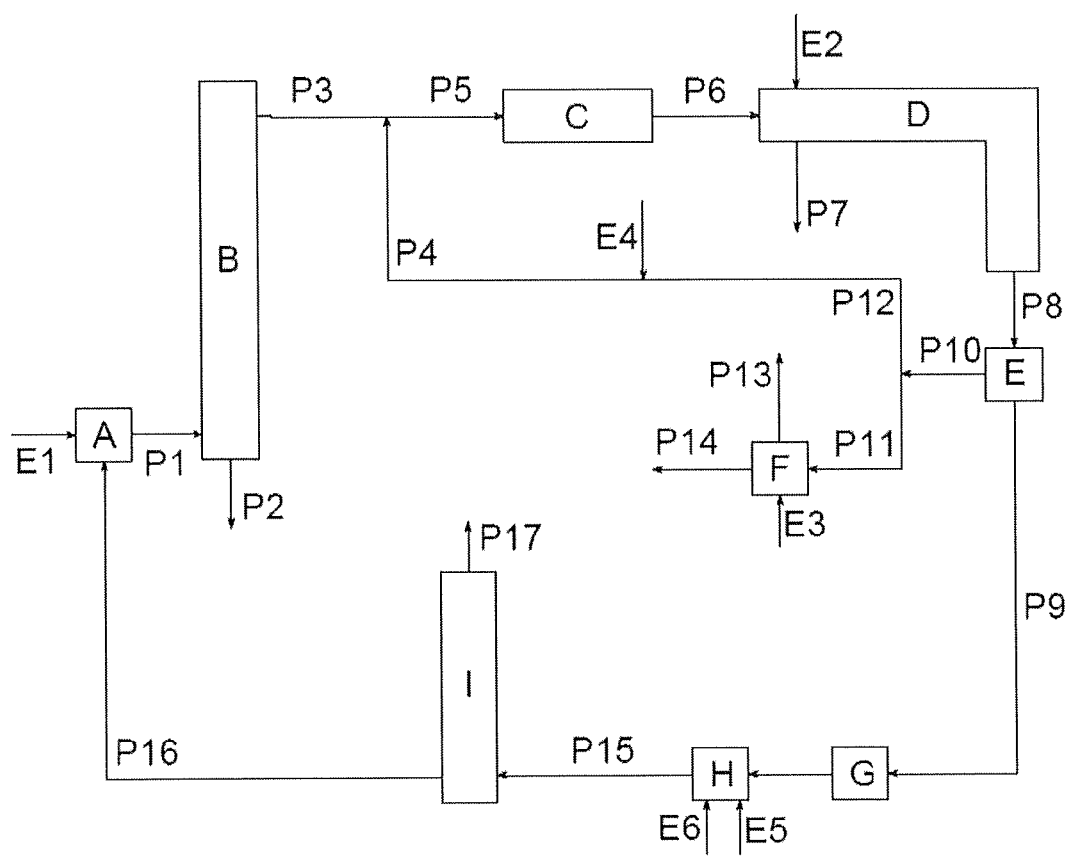
FIG. 1 shows a simplified representation, reduced to the most important steps, of the process according to the invention without compression steps and without stages for purification or drying of product streams before the use thereof in the next step.

The liquid stream P9 containing chlorine, carbon dioxide and dissolved oxygen is passed into an evaporator G and, after addition of carbon monoxide E5 and chlorine E6, is converted into phosgene in the reactor H. In this context, E5, E6 and the evaporated stream P9 can be mixed before entry into the reactor H or in the reactor H. FIG. 1 shows only the latter variant. The chlorine E6 fed in preferably comes from a chlor-alkali electrolysis and then has a low oxygen content of typically 0.1 vol. % to 2 vol. %. The carbon monoxide E5 fed in likewise contains traces of oxygen, above all if it originates from the reaction of coke with oxygen. Since the carbon monoxide is fed into the plant in a stoichiometric excess, the chlorine is predominantly to completely reacted. In addition, excess carbon monoxide reacts with the traces of oxygen present and forms carbon dioxide.

In the separating device I, the majority of the phosgene and some of the carbon dioxide is condensed out as stream P16. The gaseous stream P17 which remains is led into a waste gas treatment (not shown), since it still contains phosgene, which must be destroyed before release into the atmosphere. The destruction is conventionally carried out with water on active charcoal. With this gas stream, the majority of the carbon dioxide is removed from the system network of Deacon process and isocyanate plant, without the use of sodium hydroxide solution or other bases being necessary for this.

The liquid stream P16 is led together with the amine-containing stream E1 into the reactor A and reacted there to give the corresponding isocyanate.

Figure 2:
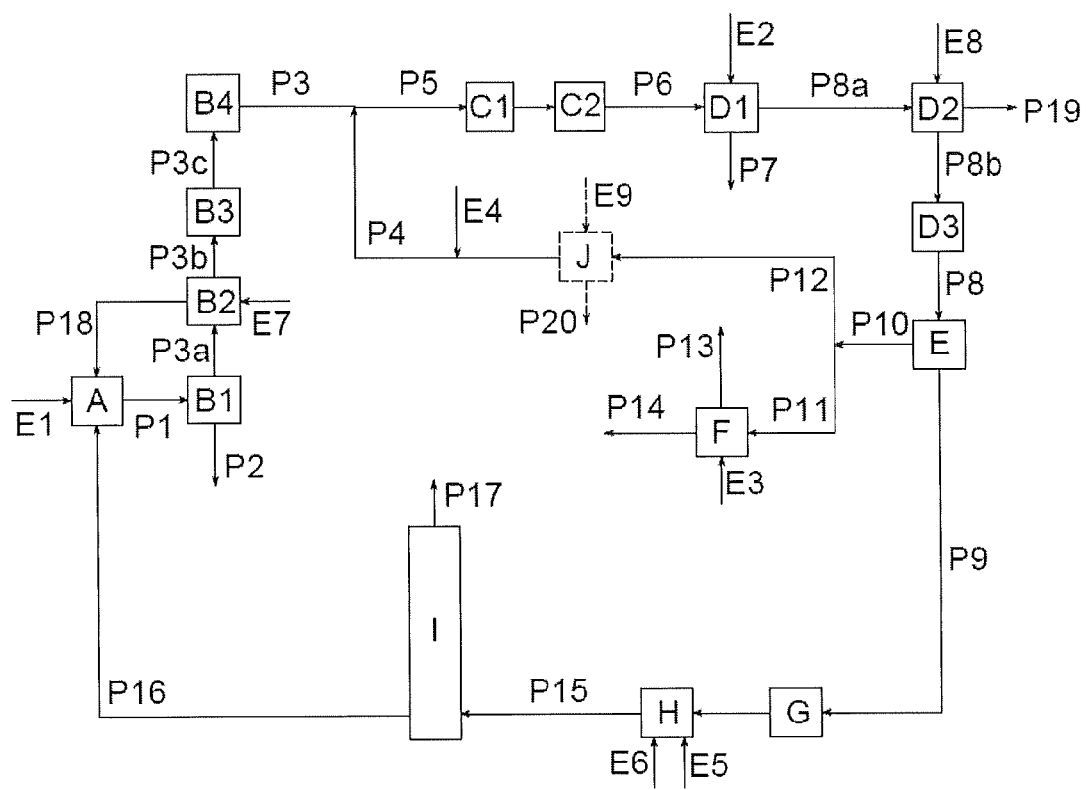
FIG. 2 shows by way of example a possible embodiment of the process according to the invention.

FIG. 2:

FIG. 2 shows a preferred embodiment of the process according to the invention. It contains all the steps from FIG. 1 and moreover shows further preferred details:

The separating device B here comprises a condenser B1, an absorber column B2, a compressor B3 and a purification stage B4. In B1, the liquid stream P2 and a gaseous stream P3a are obtained. P3a is passed into the lower part of the absorber column B2, at the top of which an organic solvent, preferably the solvent employed in the phosgenation, is fed in cold as stream E7. Further constituents, such as excess phosgene, are removed from the gas stream P3a fed in and are led back as stream P18 into the reactor A. The gas P3b emerging at the top of the absorber column B2 is led into a compressor B3 and compressed there to pressures of from 2.0 bar to 25 bar (abs.).

For further purification before the mixing with P4, the compressed gas stream P3c is led into a purification stage B4 (preferably a cold trap and/or adsorption stage, e.g. a treatment with active charcoal). A purified gaseous product stream P3 is obtained in this manner.

The oxidative process stage C here comprises a heat exchanger C1, in which the stream P5 is heated to the desired reaction temperature, and a cascade of reactors C2, in which the actual oxidation reaction takes place.

The separating device D here comprises a separation process D1, in which hydrochloric acid P7 and a gaseous stream P8a are obtained, a drying stage D2, in which the water content of the crude product gas P8a is reduced by contact with concentrated sulfuric acid E8 (preferably in a column) and a dried stream P8b, in addition to dilute sulfuric acid P19, is thus obtained, and a compressor D3, in which the gaseous product stream P8 is obtained by compression of P8b to pressures of preferably between 5.0 bar and 30 bar (abs.). The drying step D2 can alternatively also be carried out with molecular sieves or other drying agents, such as e.g. ionic liquids.

The separating device E comprises a condensation step, chlorine chiefly being removed in liquid form. In addition to oxygen, carbon dioxide is chiefly dissolved in the chlorine.

Optionally, in this embodiment, before its mixing with E4 the stream P12 is led through a wash J (shown as a broken line), in which the gas is washed with a water stream E9 to give a waste water stream P20.

Figure 3:
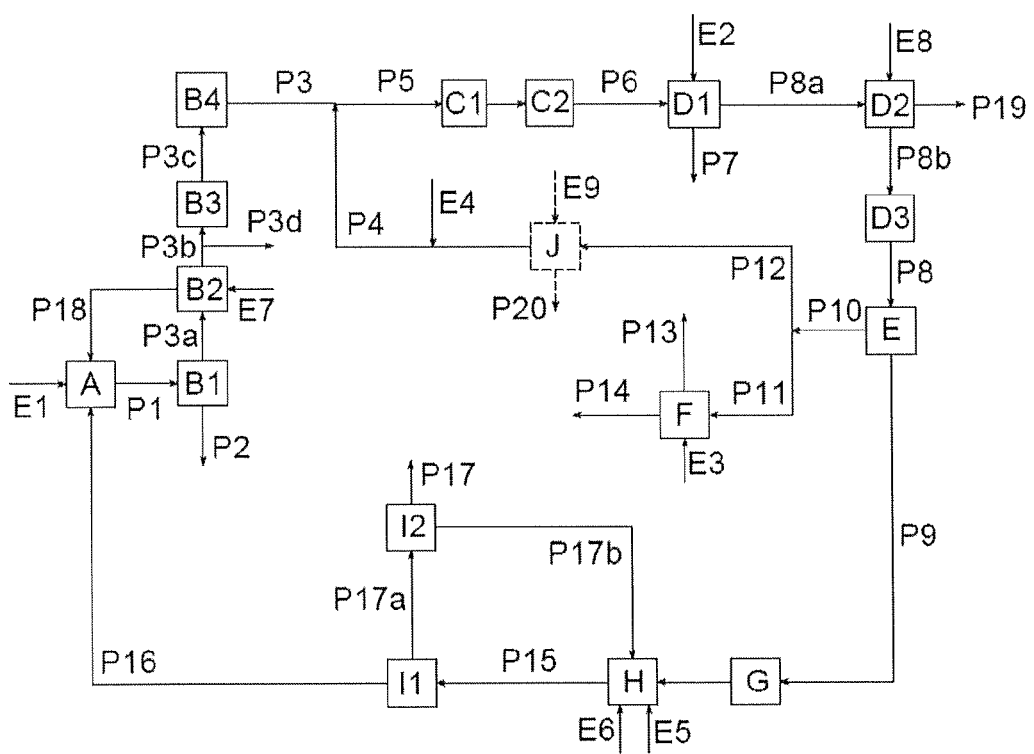
FIG. 3 shows a further possible embodiment of the process according to the invention.

FIG. 3:

FIG. 3 shows a preferred embodiment of the process according to the invention. It contains all the steps from FIG. 2 and moreover shows further preferred details:

A small part stream P3d is diverted off from stream P3b and led to a hydrogen chloride absorber (not shown) in order to produce aqueous hydrochloric acid as a by-product, e.g. for a hydrochloric acid electrolysis. In this procedure, a part of the carbon dioxide, carbon monoxide and phosgene is also sluiced out. The stream which remains is compressed in the compressor B3. This diversion of a part stream of the gas phase obtained in the separation of P1 into a hydrogen chloride absorber can also be realized without the absorption step in B2.

The separating device I here comprises two stages I1 and I2. In I1, the liquid, phosgene-rich stream P16 and a gaseous stream P17a are obtained. In I2, P17a is divided into the purge stream P17 and a stream P17b which is recycled into the reactor H.

Figure 4:
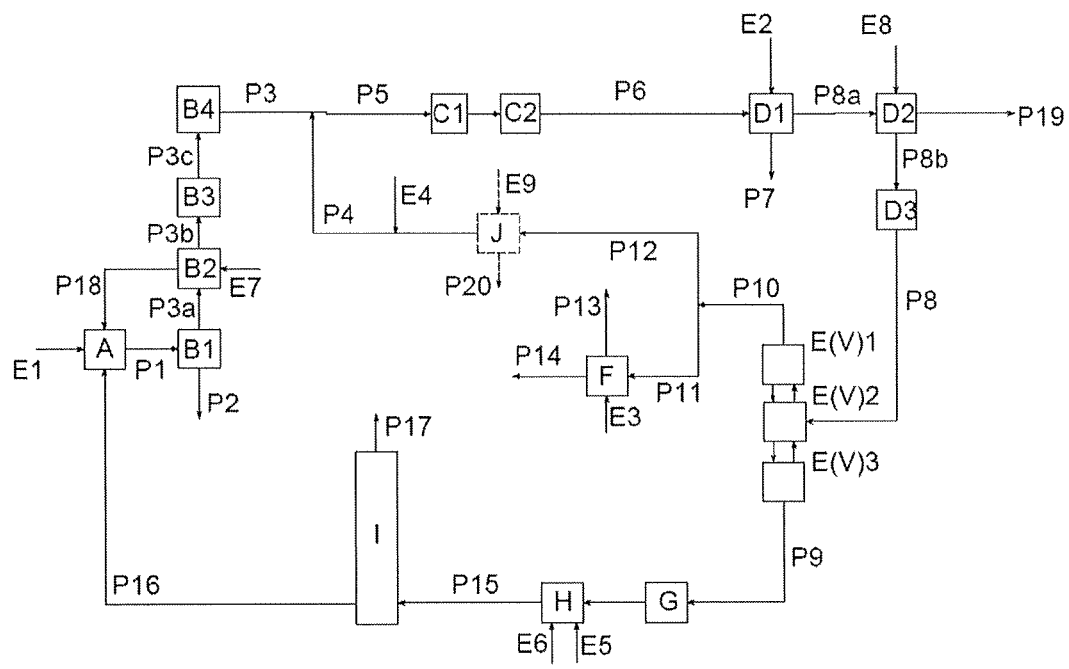
FIG. 4 shows a process according to the prior art.

FIG. 4:

The conventional mode of operation without common condensation of chlorine and carbon dioxide is described with the aid of FIG. 4. To distinguish from the figures according to the invention, apparatuses in an embodiment which is not according to the invention are identified by a "(V)" (Vergleich=Comparison) With the exception of the separating device E(V), the fundamental construction of the system corresponds to that of FIG. 2.

According to the prior art, a distillation column is employed as the separating device E(V). The overhead condenser E(V)1 removes chlorine and carbon dioxide as a liquid stream. The liquid stream trickles down the stages (indicated as E(V)2) of the distillation column and is stripped in countercurrent with vaporized chlorine. In this procedure, both the carbon dioxide and dissolved oxygen are driven out of the liquid and virtually carbon dioxide- and oxygen-free, liquid chlorine is obtained in the bottom of the distillation column. A part of this stream is led into a bottom evaporator, evaporated and introduced back into the distillation column as stripping gas. The remainder is taken off as stream P9. The gaseous stream P10 emerging from the overhead condenser E(V)1 now contains the carbon dioxide which was fed to the stage E(V) with the stream P8. The result of this is that only a relatively small content of the total carbon dioxide to be sluiced out of the system network enters into the separating device I with stream P9 via the evaporator G and the reactor H and is sluiced out with the stream P17.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

The examples were set up with a simulation tool for steady-state process simulations. The boundary conditions of the simulation are described in the following. The mass flows are scaled for all the examples such that 100 kg/h of isocyanate are produced in the reactor A.

Example 1

According to the Invention

FIG. 2 is the basis of the simulation.

With stream P16, phosgene is fed to the reactor A in an excess of 100% of the stoichiometric amount compared with the primary amine toluylenediamine (TDA) contained in the stream E1. The reaction to give toluylene-diisocyanate (TDI) is carried out at 150° C. under a pressure of 2.6 bar. The majority of the unreacted phosgene is taken off as stream P1 together with a solvent (ortho-dichlorobenzene, ODB), the TDI and the by-product HCl and cooled to 35° C. in B1. The product TDI is taken off in liquid form from B1 with the stream P2, and HCl, phosgene and further components leave the stage B1 in gaseous form with the stream P3a. P3a is brought into contact with the stream E7, which contains fresh ODB, in the absorber stage B2. In this procedure, the phosgene contained in P3a is mostly absorbed. The HCl leaves the absorber in gaseous form with the stream P3b. P3b contains, inter alia, still approx. 0.23 vol. % of phosgene, approx. 0.58 vol. % of $CO_2$ and 0.02 vol. % of CO, approx. 1.2 vol. % of $N_2$ from procedures for inertization or to maintain pressure, and traces of the solvent ODB. The majority of the solvent and of the phosgene is taken off in liquid form in the stream P18 and led back into the reactor A.

The HCl gas is compressed to 6 bar in the compressor B3 and fed as stream P3c to the purification stage B4, in which the solvent ODB is chiefly removed by adsorption on active charcoal and a purified HCl gas stream P3 is provided. An oxygen-containing return stream P4 is then admixed, so that a molar ratio of $HCl/O_2=2$ is established in the stream P5. P5 is heated to 290° C. in the heat exchanger C1 and oxidized to chlorine and water in a cascade C2 of seven adiabatically operated reactors with intermediate cooling. An HCl conversion of 85% is achieved by this procedure. Because of the oxygen excess, the phosgene and CO contained in the HCl gas are reacted to give $CO_2$.

Unreacted HCl gas and the water formed are removed in the separator D1. D1 comprises an absorption column with two packing segments arranged one above the other and material exchange trays lying above these. A separate liquid circulation trickles over each of the packing segments, and a water stream E2 is fed on to the top tray. The reaction gas P6 from C2 is led under the bottom packing segment into the separator D1. A cooled liquid circulation of 30% strength hydrochloric acid is led around this packing segment. P6 is thereby cooled and the majority of the HCl gas and of the water is separated out and removed from the bottom of D1 as a 30% strength hydrochloric acid stream P7. The residual gas enters into the top packing segment, through which a cooled 14% strength hydrochloric acid led in circulation trickles. HCl and water from the residual gas are absorbed in this hydrochloric acid. The gas emerging at the top from this packing now contains hardly any more HCl and little water. For almost complete removal of the HCl, it is led through the trays, which are charged in counter-current with a fresh water stream E2. An almost complete removal of the HCl succeeds as a result.

The gas stream P8a which has been freed from HCl and the majority of the water is then dewatered in a drying stage D2. For this, an absorber through which sulfuric acid trickles is used. Like D1, it comprises a packing part and trays arranged above this. The gas stream P8a is fed in under the packing. A cooled 78% strength sulfuric acid circulation trickles through the packing part, in which the majority of the water which remains is absorbed and is sluiced out of the bottom of D2 as a 78% strength sulfuric acid stream P19. The gas emerging from the packing is passed through the trays, which are charged in counter-current with a 96% strength sulfuric acid stream E8, so that the water is removed down to traces from the gas stream.

The dried gas stream P8b which emerges from D2 essentially contains the chlorine produced, the excess oxygen and carbon dioxide and nitrogen. It is compressed to 12 bar with the compressor D3. The stream P8 obtained in this way is then led into the condenser E and cooled to −40° C. In this procedure, 99.8% of the chlorine produced in C2 and a part of the carbon dioxide condense. The oxygen contained in P8 dissolves in traces in the condensate. The condensate stream P9 formed in this way contains approx. 1.15% by weight of $CO_2$ and approx. 800 ppm of oxygen. The gas stream P10 which remains leaves the condenser E. P10 includes the excess oxygen, the nitrogen, the residual, non-condensed chlorine and carbon dioxide. To remove inert substances and secondary components, a part stream P11 of the gas stream P10 which remains is sluiced out. P11 is passed into the waste gas treatment stage F and dechlorinated there with a stream E3 containing sodium hydroxide solution. The carbon dioxide contained in P11 is likewise reacted with the sodium hydroxide solution from E3. Approx. 10% of the total carbon dioxide sluiced out is removed at this point in this manner. The purified, chlorine- and carbon dioxide-free gas stream P13 and the waste water P14 leave F. P14 contains the carbon dioxide which has reacted with sodium hydroxide solution to give sodium carbonate, and the chlorine which has been converted into NaCl and NaOCl.

The gas stream P12 which remains after removal of the part stream P11 can optionally be washed and remoistened again with a water stream E9 in a washing stage J. Excess wash water leaves this stage as stream P20. The washed gas stream is now mixed with fresh oxygen E4 and then mixed as oxygen-containing return stream P4 with the purified HCl gas stream P3.

The condensate stream P9 is evaporated in the evaporator G and passed into the reactor H. An additional chlorine stream E6 is also passed in there, which compensates the losses (e.g. in the sluiced-out stream P11 or the HCl which has not reacted in C2). E6 originates from a chlor-alkali electrolysis and is contaminated with 0.2 vol. % of oxygen. For the preparation of phosgene, a CO stream E5 is furthermore fed to H. E5 also contains oxygen (0.1 vol. %) as a secondary component. In order to react all the chlorine in the preparation of phosgene, CO is fed into the reactor in a 6% stoichiometric excess. The oxygen contained in E5, E6 and P9 is reacted with a part of the CO in a secondary reaction to give carbon dioxide. The stream P15 includes the phosgene produced in H and is cooled to −25° C. under 1.6 bar in the condenser I, 98.8% of the phosgene produced in H and a part of the carbon dioxide condensing and leaving the condenser as stream P16 with approx. 0.51 wt.% of $CO_2$. Traces of CO are also dissolved in P16. The gas phase which remains with the residual phosgene, the CO and further inert substances and secondary components is sluiced out as waste gas stream P17. The remainder of the carbon dioxide to be sluiced out is removed at this point.

Example 2

According to the Invention

FIG. 3 is the basis of the simulation.

Example 2 contains the same steps as Example 1, but a part of the HCl gas is additionally diverted from the absorber B2 and led to an HCl absorber (not shown). A part of the stream which leaves the condensation step I in gaseous form and contains the CO excess is furthermore recycled into the reactor H.

Stages A, B1 and B2 are operated just as described in Example 1. The HCl leaves the absorber in gaseous form with the stream P3b. P3b contains, inter alia, still approx. 0.24 vol. % of phosgene, approx. 1.2 vol. % of $N_2$ from procedures for inertization or to maintain pressure, and traces of the solvent ODB. Its content of $CO_2$ of 1.5 vol. %, however, is now significantly higher than in Example 1, since by feeding back in the condensation step I1/I2 the amount sluiced out there has become smaller and a concentration thus occurs. On the other hand, CO still occurs only in traces. 10% of P3b is sluiced out as stream P3d and led to an HCl absorber (not shown). A part of the phosgene contained in P3b and of the $N_2$ and approx. 30% of the total $CO_2$ to be sluiced out are thereby removed.

The gas stream which remains is compressed to 6 bar in the compressor B3 and led as stream P3c into the purification stage B4.

The solvent ODB is chiefly removed from stream P3c in the purification stage B4 by adsorption on active charcoal and a purified HCl gas stream P3 is provided. An oxygen-containing return stream P4 is then admixed, so that a molar ratio of $HCl/O_2=2$ is established in the stream P5.

Stages C1, C2, D1, D2, D3 and E are also operated as described in Example 1. 99.8% of the chlorine produced in C2 is again condensed in P9. However, since the $CO_2$ concentration in P3c is already higher, P9 also has a higher $CO_2$ content than in Example 1, namely 2.4% by weight. The oxygen content is 740 ppm.

The gas stream P10 which remains leaves the condenser E and is in turn partly sluiced out as in Example 1. By this sluicing out, approx. 20% of the $CO_2$ to be sluiced out is now removed, since the sluicing-out stream also has a higher $CO_2$ concentration. The treatment of the sluicing-out stream in F and of the remaining gas stream in the optional stage J and subsequent mixing thereof with fresh oxygen E4 and feeding back as oxygen-containing stream P4 into the purified HCl gas stream P3 are carried out as described in Example 1.

As in Example 1, the condensate stream P9 is evaporated in the evaporator G and passed into the reactor H. The additional chlorine stream E6 is now greater than in Example 1, since in addition to the losses in the sluicing-out stream P11 and the HCl which has not reacted in C2, the HCl sluicing-out stream P3d must also be compensated. E6 originates from a chlor-alkali electrolysis and is contaminated with 0.2 vol. % of oxygen. For the preparation of phosgene, the CO stream E5 with 0.1 vol. % of oxygen as a secondary component is in turn fed to H. In order to react all the chlorine in the preparation of phosgene, CO is present in a 6% stoichiometric excess at the intake of reactor H. Since a part of the gas stream P17a removed in the condensation stage I1 downstream of the reactor H is recycled, only approx. 95.4% of the CO required must still be provided with E5. The CO stream E5 fed in is therefore smaller than in Example 1. The oxygen contained in E5, E6 and P9 is reacted with a part of the CO in a secondary reaction to give carbon dioxide. The stream P15 includes the phosgene produced in H and is cooled to −25° C. under 1.6 bar in the condenser I1, 99.8% of the phosgene produced in H and a part of the carbon dioxide condensing and leaving the condenser as stream P16 with approx. 1.3% by weight of $CO_2$. The $CO_2$ content is higher than in Example 1, because $CO_2$ is likewise led back into the reactor H with the return feed and is concentrated in this way. Traces of CO are dissolved in P16. The gas phase which remains with the residual phosgene, the CO and further inert substances and secondary components is taken off as gas stream P17a. P17a is divided in I2, 10% is sluiced out as stream P17, the remainder is led back into the reactor H as stream P17b. The remainder of the carbon dioxide to be sluiced out is removed here in this manner.

Example 3

Comparison Example

FIG. 4 is the basis of the simulation.

Example 3 contains the same steps as Example 1, but E is now configured as a distillation column in order to free the liquid chlorine removed from $CO_2$ and dissolved oxygen.

Stages A, B1, B2, B3 and B4 are operated just as described in Example 1. The HCl leaves the absorber B2 in gaseous form with the stream P3b. P3b contains, inter alia, still approx. 0.22 vol. % of phosgene, approx. 1.2 vol. % of $N_2$ from procedures for inertization or to maintain pressure, and traces of the solvent ODB. Its content of $CO_2$ and CO of 0.15 vol. % ($CO_2$) and 0.03 vol. % (CO) is very much lower than in Example 1, since due to the distillation of the liquid chlorine essentially no $CO_2$ and no oxygen is passed with the stream P9 into the phosgene preparation step H.

The gas stream P3b is compressed to 6 bar in the compressor B3 and led as stream P3c into the purification stage B4.

The solvent ODB is chiefly removed from stream P3c in the purification stage B4 by adsorption on active charcoal and a purified HCl gas stream P3 is provided. An oxygen-containing return stream P4 is then admixed, so that a molar ratio of $HCl/O_2=2$ is established in the stream P5.

Stages C1, C2, D1, D2 and D3 are also operated as described in Example 1.

The stage E is now configured as a distillation column. It comprises an overhead condenser E(V)1, the distillation stages E(V)2 on to which the stream P8 is led, and the bottom evaporator E(V)3. Cooling to −40° C. is effected in the overhead condenser E(V)1 and the bottom evaporator E(V)3 evaporates approx. ⅓ of the amount of the stream P8 fed in. A bottom stream P9 in which 99.7% of the chlorine produced in C2 is removed thus results. P9 still contains only 0.17% by weight of $CO_2$ and no further oxygen.

The gas stream P10 which remains leaves the distillation column E at the overhead condenser E(V)1 and is in turn partly sluiced out as in Example 1. Approx. 70% of the $CO_2$ to be sluiced out is thereby now removed, since due to the distillation scarcely any $CO_2$ is removed with the liquid chlorine and it is therefore concentrated in the return feed.

The treatment of the sluicing-out stream in F and of the remaining gas stream in the optional stage J and subsequent mixing thereof with fresh oxygen E4 and feeding back as oxygen-containing stream P4 into the purified HCl gas stream P3 are carried out as described in Example 1.

As in Example 1, the condensate stream P9 is evaporated in the evaporator G and passed into the reactor H. The additional chlorine stream E6 originates from a chlor-alkali electrolysis and is contaminated with 0.2 vol. % of oxygen. For the preparation of phosgene, the CO stream E5 with 0.1 vol. % of oxygen as a secondary component is in turn fed to H. In order to react all the chlorine in the preparation of phosgene, CO is present in a 6% stoichiometric excess at the intake of reactor H.

The oxygen contained in E5 and E6 is reacted with a part of the CO in a secondary reaction to give carbon dioxide. The stream P15 includes the phosgene produced in H and is cooled to −25° C. under 1.6 bar in the condenser I1, 99% of the phosgene produced in H and a part of the carbon dioxide condensing and leaving the condenser as stream P16 with approx. 0.13% by weight of $CO_2$. Traces of CO are also dissolved in P16. The gas phase which remains with the residual phosgene, the CO and further inert substances and secondary components is sluiced out as gas stream P17. The remainder of the carbon dioxide to be sluiced out is removed here in this manner. The following overview compares the essential simulation results with one another:

|  | Example 1 (FIG. 2) | Example 2 (FIG. 3) | Example 3 (FIG. 4) |
| --- | --- | --- | --- |
| Proportion of the $CO_2$ sluiced out via the waste gas treatment F (stream P11) in relation to the total $CO_2$ sluiced out | 9% | 18% | 70% |

|  | Example 1 (FIG. 2) | Example 2 (FIG. 3) | Example 3 (FIG. 4) |
|---|---|---|---|
| Proportion of the $CO_2$ sluiced out via the separating device I (stream P17) in relation to the total $CO_2$ sluiced out | 91% | 52% | 30% |
| Proportion of the $CO_2$ sluiced out via sluiced-out HCl gas (stream P3d) in relation to the total $CO_2$ sluiced out | — | 30% | — |
| NaOH consumption (stream E3) in the waste gas treatment F compared with Example 3 | 33% | 41% | 100% |
| Refrigeration capacity in the separating device E for condensation of the chlorine compared with Example 3 | 74% | 70% | 100% |

As can be seen from the overview, the NaOH consumption is reduced considerably with the process according to the invention. Furthermore, less refrigeration capacity is required to remove the chlorine, since in the distillation column of Example 3 the chlorine evaporated in the bottom with the $CO_2$ driven out must be condensed.

The invention claimed is:

1. A process for preparing an isocyanate comprising the steps of
   (i) reacting a stream E1 comprising a primary amine with a phosgene-comprising stream P16 to form a product stream P1, which comprises said isocyanate, hydrogen chloride, unreacted phosgene, and carbon oxides;
   (ii) separating the product stream P1 into a liquid product stream P2 comprising said isocyanate and a gaseous product stream P3 comprising hydrogen chloride, unreacted phosgene, and carbon oxides;
   (iii) mixing the product stream P3 with a gaseous product stream P4 comprising oxygen to form a gaseous mixed stream P5;
   (iv) oxidizing the gaseous mixed stream P5 on a catalyst to form a gaseous product stream P6 comprising hydrogen chloride, carbon dioxide, excess oxygen, chlorine, and water;
   (v) partially to completely removing the hydrogen chloride and water from stream P6 as a stream P7 comprising hydrochloric acid to form a product stream P8 depleted in hydrogen chloride and water;
   (vi) separating the product stream P8 into a liquid chlorine-rich product stream P9, which comprises chlorine, carbon dioxide, and oxygen, and a gaseous, low-chlorine product stream P10, which comprises the residual amount of chlorine from P8 not contained in P9, carbon dioxide, and oxygen;
   (vii) dividing the gaseous product stream P10 into a gaseous purge stream P11 and a gaseous product stream P12;
   (viii) treating the purge stream P11 with an aqueous base E3 to form a gaseous purge stream P13 and a liquid waste water stream P14;
   (ix) mixing the gaseous stream P12 with a gaseous stream E4 comprising oxygen to form the gaseous product stream P4 which comprises oxygen and is employed in step (iii);
   (x) evaporating the liquid chlorine-rich product stream P9 to form a gaseous chlorine-rich product stream and mixing the gaseous chlorine-rich product stream with carbon monoxide E5 and with chlorine E6 to give a mixture, and reacting said mixture to give a gaseous product stream P15 comprising phosgene and carbon oxides;
   (xi) separating the gaseous product stream P15 in a separating device I into a phosgene-rich product stream P16, which is employed in step (i) and comprises phosgene and carbon oxides, and into a low-phosgene purge stream P17 which comprises the residual amount of the phosgene from P15 which is not contained in P16 and carbon oxides;
   wherein
   in step (vi) the separation of the product stream P8 into a liquid chlorine-rich product stream P9 and into a gaseous low-chlorine product stream P10 is carried out by cooling P8 to a temperature of from −10° C. to −80° C. under an absolute pressure of from 1 bar to 30 bar without subsequent distillation.

2. The process of claim 1, wherein, in step (xi), from 35% to 99% of the total carbon dioxide to be sluiced out is sluiced out via the purge stream P17.

3. The process of claim 1, wherein, in step (ii), P1 is divided into the liquid product stream P2 comprising said isocyanate and a gaseous stream, wherein a portion of said gaseous stream is sluiced out and passed into a hydrogen chloride absorber, and wherein the remaining portion of said gaseous stream is treated further as stream P3 in step (iii).

4. The process of claim 1, wherein, in step (v), the partial to complete removal of the hydrogen chloride and of the water from P6 is realized by treatment of P6 with an absorption agent chosen from water or 1 to 20% strength hydrochloric acid.

5. The process of claim 1, wherein, in step (vii), the gaseous product stream P10 is divided into a gaseous purge stream P11 and into a gaseous product stream P12 in a weight ratio of P12:P11 averaged over time of from 100:1 to 5:1.

6. The process of claim 1, wherein, in step (viii), an aqueous alkali metal or alkaline earth metal hydroxide solution is used as the aqueous base E3.

7. The process of claim 1, wherein the gaseous product stream P12 is led through a wash in which the gas is washed and only thereafter is mixed in step (ix) with a gaseous stream E4 comprising oxygen.

* * * * *